United States Patent
Yuan et al.

(10) Patent No.: US 10,522,426 B1
(45) Date of Patent: Dec. 31, 2019

(54) HAZE MASK SYSTEM FOR HAZE SUPPRESSION

(71) Applicant: KLA-TENCOR CORPORATION, Milpitas, CA (US)

(72) Inventors: Hongxing Yuan, San Ramon, CA (US); Dimitry Pokras, San Jose, CA (US); William VanHoomissen, San Jose, CA (US); Douglas Chan, San Francisco, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 16/271,506

(22) Filed: Feb. 8, 2019

(51) Int. Cl.
    *G01N 21/00* (2006.01)
    *H01L 21/66* (2006.01)
    *G01B 11/30* (2006.01)

(52) U.S. Cl.
    CPC .............. *H01L 22/12* (2013.01); *G01B 11/30* (2013.01)

(58) Field of Classification Search
    CPC .. G01N 21/9501; G01N 21/94; G01N 21/956; G01N 2021/95676; G03F 1/84
    USPC ............................................ 356/237.1–237.5
    See application file for complete search history.

(56) References Cited

U.S. PATENT DOCUMENTS

| 3,545,854 | A  |   | 12/1970 | Olsson |         |
|-----------|----|---|---------|--------|---------|
| 7,796,249 | B2 | * | 9/2010  | Wang   | G03F 1/84 |
|           |    |   |         |        | 356/237.1 |
| 7,839,495 | B2 |   | 11/2010 | Baran et al. | |
| 8,891,079 | B2 |   | 11/2014 | Zhao et al. | |
| 8,974,988 | B2 |   | 3/2015  | Lin et al. | |
| 2016/0266503 | A1 | * | 9/2016 | Van Voorst | G01B 11/00 |

OTHER PUBLICATIONS

New Product: Haze Removal System PROMAHAZE, Lasertec Corporation, Sep. 12, 2009, https://www.lasertec.co.jp/en/topics/2009/091112.html.
Kishkovich, et al., Reticle haze control: Global update and technology roadmap, Solid State Technology, Aug. 24, 2010, https://electroiq.com/2010/08/reticle-haze_control/.
Meli et al., Detection of Printable EUV Mask Absorber Defects and Defect Adders by Full Chip Optical Inspection of EUV Patterned Wafers, Annual Semi Advanced Semiconductor Manufacturing Conference, 2016, IEEE.
Wocko et al., Study of Relationship Between 300 mm Si Wafer Surface and Annealing Temperatures for Advanced Semiconductor-Based Applications, Annual Semi Advanced Semiconductor Manufacturing Conference, 2010, IEEE.

* cited by examiner

*Primary Examiner* — Hoa Q Pham
(74) *Attorney, Agent, or Firm* — Hodgson Russ LLP (57) ABSTRACT

This system and method minimize an effect of haze to signal-to-noise ratio and compensate for haze on the haze map. A first mask with a first aperture is disposed along the path of the light beam between a light source and a collector. A first actuator moves the first mask along a tangential direction. A second mask with a second aperture is disposed along the path of the light beam between the first mask and the collector. A second actuator moves the second mask along a radial direction perpendicular to the tangential direction. The first mask and the second mask are independently movable along the tangential direction and the radial direction using the first actuator and the second actuator.

14 Claims, 6 Drawing Sheets

| PSL size (nm) | Mask changer only | M1 mask only | Mask changer +M1 mask |
|---|---|---|---|
| 83 | 29.89 | 33.95 | 35.8 |
| 102 | 234.1 | 264.4 | 280.9 |
| 126 | 1211 | 1364 | 1495 |
| Haze | 0.023 | 0.0208 | 0.0163 |

FIG. 7

HAZE MASK SYSTEM FOR HAZE SUPPRESSION

FIELD OF THE DISCLOSURE

This disclosure relates to haze suppression during imaging.

BACKGROUND OF THE DISCLOSURE

Evolution of the semiconductor manufacturing industry is placing greater demands on yield management and, in particular, on metrology and inspection systems. Critical dimensions continue to shrink, yet the industry needs to decrease time for achieving high-yield, high-value production. Minimizing the total time from detecting a yield problem to fixing it determines the return-on-investment for a semiconductor manufacturer.

Fabricating semiconductor devices, such as logic and memory devices, typically includes processing a semiconductor wafer using a large number of fabrication processes to form various features and multiple levels of the semiconductor devices. For example, lithography is a semiconductor fabrication process that involves transferring a pattern from a reticle to a photoresist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer that are separated into individual semiconductor devices.

Metrology processes are used at various steps during semiconductor manufacturing to monitor and control the process. Metrology processes are different than inspection processes in that, unlike inspection processes in which defects are detected on wafers, metrology processes are used to measure one or more characteristics of the wafers that cannot be determined using existing inspection tools. Metrology processes can be used to measure one or more characteristics of wafers such that the performance of a process can be determined from the one or more characteristics. For example, metrology processes can measure a dimension (e.g., line width, thickness, etc.) of features formed on the wafers during the process. In addition, if the one or more characteristics of the wafers are unacceptable (e.g., out of a predetermined range for the characteristic(s)), the measurements of the one or more characteristics of the wafers may be used to alter one or more parameters of the process such that additional wafers manufactured by the process have acceptable characteristic(s).

In the semiconductor industry, the term haze can be used to describe the micro-roughness of a wafer surface. This can be a useful parameter for both integrated circuit and wafer manufacturers. Background scatter caused by imperfections on the surface of the substrate, such as intrinsic substrate roughness and polishing damage, leads to haze. Haze has been shown to correlate to a broad array of process parameters, such as surface roughness, grain size, and process temperature.

Many metrology tools and other tools in the semiconductor industry include an ultraviolet (UV) channel and an additional second wavelength or dual wavelength (DW) channel with a longer wavelength to detect the embedded defects within the photo-resistors or multi-layered structure for memory. For example, a longer wavelength of 488 nm may be used. There is no effective way to suppress the haze with the UV channel. Therefore, new techniques and systems to suppress haze are needed.

BRIEF SUMMARY OF THE DISCLOSURE

A system is provided in a first embodiment. The system comprises an illumination subsystem that generates a light beam, a stage configured to hold a wafer in a path of the light beam, a collector in the path of the light beam, a first mask disposed along the path of the light beam between the light source and the collector, a first actuator that moves the first mask along a tangential direction, a second mask disposed along the path of the light beam between the first mask and the collector, and a second actuator that moves the second mask along a radial direction perpendicular to the tangential direction. The first mask defines a first aperture. The second mask is fabricated of metal and defines a second aperture. The first mask and the second mask are independently movable along the tangential direction and the radial direction, respectively, using the first actuator and the second actuator to minimize an effect of haze to signal-to-noise ratio.

The system can include a processor in electronic communication with the first actuator and the second actuator. The processor can be configured to determine a haze map of the wafer and send instructions to at least one of the first actuator and the second actuator to move at least one of the first mask or the second mask.

In an instance, the processor is further configured to send instructions to the second actuator to sweep the second mask over a range, monitor signal-to-noise ratio and haze values, and determine an optimal position for the second mask that minimizes the effect of haze to signal-to-noise.

In an instance, the processor is further configured to send instructions to the first actuator to sweep the first mask over a range, monitor signal-to-noise ratio and haze values, and determine an optimal position for the first mask that minimizes the effect of haze to signal-to-noise.

The first actuator may include a mask change wheel.

The first mask may be disposed on a mask change wheel. The mask change wheel can include a plurality of other masks.

A method is provided in a second embodiment. The method comprises disposing, using a first actuator, a first mask at a first position along a path of a light beam between a light source and a collector. The first mask defines a first aperture. Using a second actuator, a second mask is disposed at a second position along the path of the light beam between the first mask and the collector. The second mask is fabricated of metal. The second mask defines a second aperture. The first position and the second position minimize an effect of haze to signal-to-noise ratio.

Disposing the first mask may be independent of disposing the second mask.

In an instance, a haze map of the wafer is determined using a processor. Instructions are sent, using the processor, to at least one of the first actuator and the second actuator to move at least one of the first mask or the second mask to compensate for haze on the haze map.

In an instance, instructions can be sent from the processor to the second actuator to sweep the second mask over a range. Using the processor, the signal-to-noise ratio and haze values are monitored. Using the processor, an optimal position for the second mask that minimizes the effect of haze to signal-to-noise can be determined.

In an instance, instructions can be sent from the processor to the first actuator to sweep the first mask over a range.

Using the processor, the signal-to-noise ratio and haze values can be monitored. Using the processor, an optimal position for the first mask that minimizes the effect of haze to signal-to-noise can be determined.

Disposing the first mask may include moving the first mask in a tangential direction.

Disposing the second mask may include moving the second mask in a radial direction perpendicular to the tangential direction.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

To detect embedded defects, such as those in a 3D NAND film stack (e.g., an ONON stack), an additional channel with a particular wavelength or DW channel, besides the UV channel, can be used. To achieve better sensitivity, tighter haze control is needed to minimize negative haze impact and improve signal-to-noise ratio. As seen in the example shown in FIG. 1, the haze in the exemplary haze map is not insignificant. However, there is usually residual alignment error for both illumination and collection, and the resultant haze distribution may vary from tool to tool as the typical haze map shown in FIG. 1, where the hot spots are shifted to the right side. A haze map is far field projection of intrinsic haze of a wafer when it is illuminated with certain of certain spot size and wavelength. Ideally, the hot spots on the haze map formed as the result of larger tangential illumination numerical aperture are centered on the map.

Figure 2:
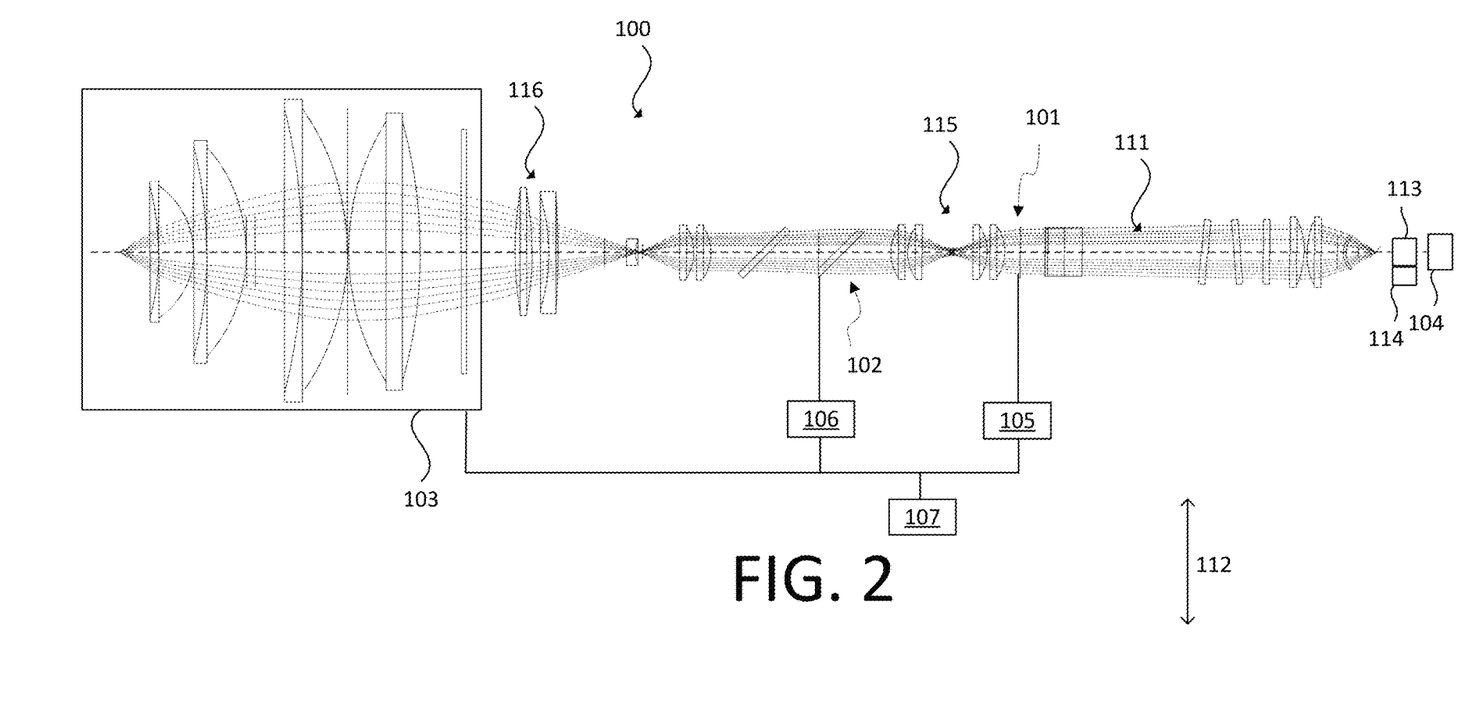
FIG. 2 is a block diagram of an embodiment of a system in accordance with the present disclosure.

A dynamic and reconfigurable haze mask combination that uses two masks is disclosed in the embodiments herein. An embodiment of a system 100 is shown in FIG. 2. The system 100 includes an illumination subsystem 104 that generates a light beam 111 to illuminate defects on a wafer 113 and scattering light from the wafer. The system 100 also includes a stage 114 configured to hold the wafer 113 in a path of the light beam 111. While FIG. 2 illustrates the light beam 111 as passing through the wafer 113 in a linear manner, the light beam 111 may be projected at the wafer 113 at an angle and reflected from the wafer 113 at an angle toward the first mask 101. The system 100 also includes a collector 103. The collector 103 is in the path of the light beam 111. The collector 103 can include one or more lenses and a sensor.

For UV channels, a P-lens is not present, which is pneumatically actuated. For DW channel, a P-lens 116 is present. All lenses in FIG. 2 may have a dual band antireflective coating for UV and DW. There is no impact to haze mask. For haze mapping, both slits from first mask 101 and second mask 102 are mechanical slits, and they are wavelength independent.

A first mask 101 is disposed along the path of the light beam 111 between the illumination subsystem 104 and the collector 103. The first mask 101 defines a first aperture. The first mask 101 can be fabricated from a steel sheet. For example, the first mask 101 may be a 302 stainless steel sheet.

Figure 1:
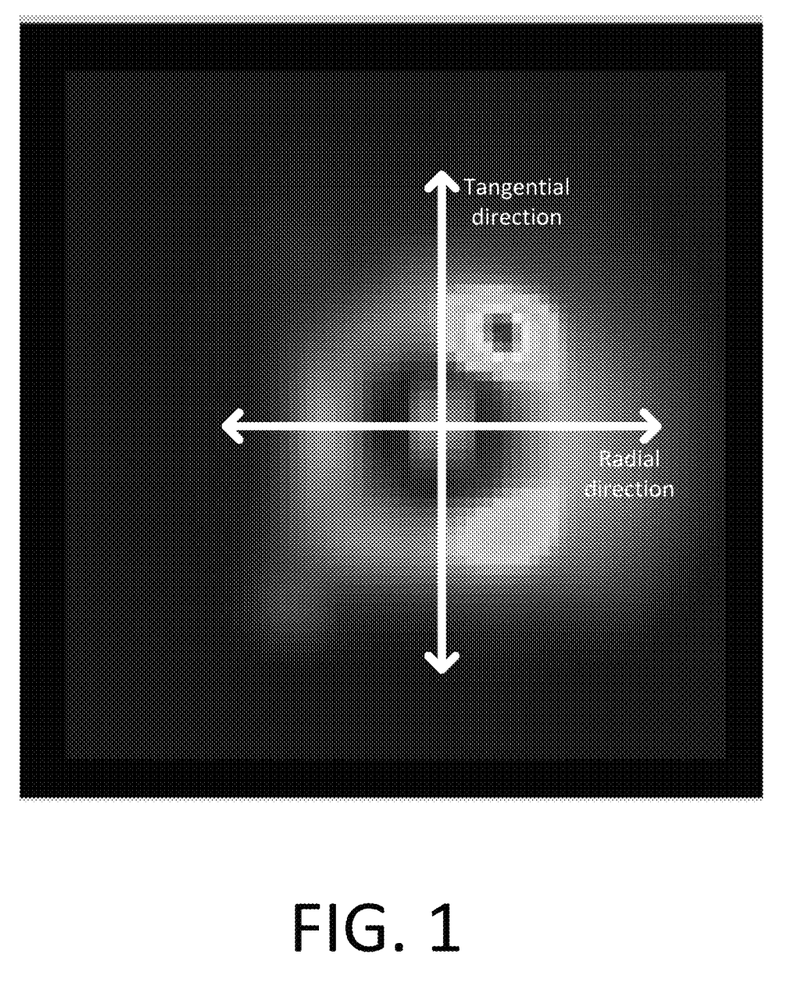
FIG. 1 is an exemplary haze map for the second wavelength channel with square DCC shadow in the center and with radial and tangential directions designated.

A first actuator 105 moves the first mask 101 in the tangential direction (as seen in FIG. 1). The first actuator can be a mask change wheel. Any angular position for the first mask 101 can be obtained using the first actuator 105. The first actuator 105 can provide an acceptable level of precision. In an instance, the first actuator 105 is a stepper motor with an encoder.

In an instance, the first mask 101 is disposed on a mask change wheel. The first mask 101 is one of several masks on the mask change wheel. The mask change wheel can select a mask that provides optimized haze reduction. The masks on the mask change wheel, including the first mask 101, can be used for a DW channel.

Figure 3:
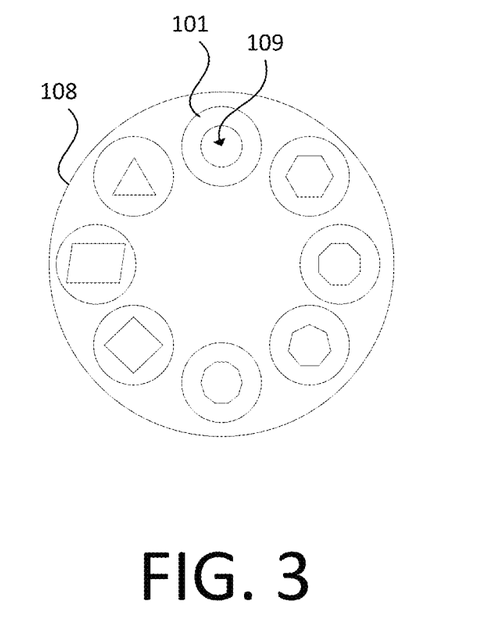
FIG. 3 is a perspective view of an embodiment of the first mask of FIG. 2.

FIG. 3 is a perspective view of an embodiment of the first mask 101 of FIG. 2. The first mask 101 is part of the mask change wheel 108. The first mask 101 includes a first aperture 109, which in this instance is circular. Other shapes are possible. The other masks on the mask change wheel 108 include apertures with different shapes (e.g., polygonal, arcuate, etc.). While eight masks are illustrated in the mask change wheel 108, more or fewer masks are possible. In an instance, ten masks are included on the mask change wheel.

Regarding the mask change wheel 108, the different sizes and shapes of masks can be combined with the first mask 101. The various masks in the mask change wheel 108 can be formed from a thin metal sheet, such as a steel sheet.

An extra haze mask on the mask changer may be fixed to the place holder of the mask changer. Thus, impact to the UV channel can be minimized.

Turning back to FIG. 1, a second mask 102 is disposed along the path of light beam 111 between the first mask 101 and the collector 103. Relay lenses 115 may be disposed between the first lens 101 and the second lens 102. Four of the relay lenses are illustrated, but other numbers are possible. The second mask 102 is fabricated of metal and defines a second aperture. For example, the second mask 102 may be fabricated of 302 stainless steel. The number of apertures in the second mask 102 can vary. More of fewer apertures than illustrated herein are possible. Thus, the second mask 102 may have only one aperture.

The second mask 102 may be an oversize of the original mirror made from fused silica. The second mask 102 can keep most of area open to remove the impact to UV. However, to achieve the haze mapping for both UV and DW, a mechanical slit can be formed to overlap with original coated slit on mirror. At the same time, an additional mask is formed to block haze. The additional mask is an elliptical disk in this instance.

In an instance, the second mask 102 includes a thin metal sheet that is overlapped and fixed to a mirror. This can reduce negative effects to the UV channel. The mirror may be held down by a retainer frame. The metal sheet can be added between the mirror and the retainer frame. Thus, the metal sheet can be held between the mirror and the retainer frame.

Figure 4:
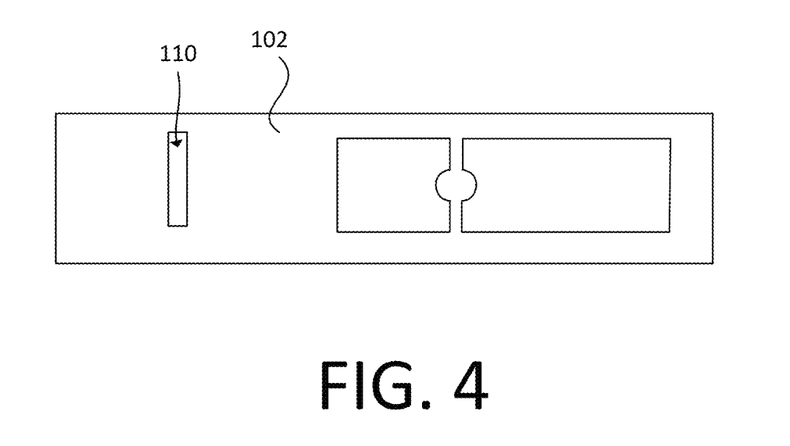
FIG. 4 is a perspective view of an embodiment of the second mask of FIG. 2.

FIG. 4 is a perspective view of an embodiment of the second mask 102 of FIG. 2. The second mask 102 can include a second aperture 110 in a mirror. As seen in FIG. 4, the second mask 102 can include an oval mask and a slit mask. The oval mask and the slit mask can be formed in the same piece. The second mask 102 can enable the haze mapping for both UV and DW.

Regarding the mirror, there can be a mechanical slit on the second mask 102. It should be aligned with optical slit formed with coating on the mirror to allow both UV and DW light to pass through to enable haze mapping for both UV and DW. The elliptical disk mask may be positioned so that it locates in the unoccupied area of UV and can be movable by motorized actuation.

Turning back to FIG. 1, a second actuator 106 moves the second mask 102 along a radial direction perpendicular to the tangential direction (as seen in FIG. 1). The second actuator 106 can move the second mask 102 along a whole length of its mirror with an acceptable level of precision. In an instance, the second actuator 106 includes two pneumatic cylinders that operate in opposite directions.

The first mask 101 and the second mask 102 are independently movable along the radial direction (e.g., direction 112) and the tangential direction (e.g., perpendicular to direction 112, such as going into the page) using the first actuator 105 and the second actuator 106. The radial direction also may extend in other directions, and direction 112 is only one example. Thus, the first mask 101 and second mask 102 are dynamic and reconfigurable for different wafers or applications to adapt to the different offsets of hot spots of haze that result from residual alignment errors and intrinsic properties of different wafers.

The first mask 101 and the second mask 102 can be positioned along the tangential direction and radial directions independently, so haze with shifted hot spots can be compensated for by reconfiguring the position of the first mask 101 and the second mask 102 to minimize the detrimental effect of haze to signal-to-noise ratio and to improve the sensitivity.

Natural variation of haze "hot spots" can shift between tools, such as metrology tools. To suppress the haze, dynamic and adaptive haze masks with particular sizes and shapes can be used. The first actuator 105 and second actuator 106 can independently provide radial motion of second mask 102 and tangential motion of the first mask 101. The second mask 102 and first mask 101 may be considered conjugated, and the combination of independent first mask 101 and second mask 102 can be adaptive to different haze distributions of different tools by selecting the mask shape and size for the first mask 101 and second mask 102.

To reduce impact of two extra masks to original UV channels, a desired pattern is cut from a thin metal sheet, and it is overlapped with a mirror to form the second mask 102. In addition, the original slit formed by dedicated design of coating for UV channel may not be effective for DW because the slit on the mirror may be formed with an optical coating for UV. The optical coating may be transparent at DW, which means the optical coating cannot be used to map haze for DW. Thus, mapping haze for DW may be difficult without the second mask 102. As shown in FIG. 2, the first mask 101 and second mask 102 are combined together, which reduces impact to UV channels. The size of the haze mask can be configured to block the possible "hot spots" of haze, and its location can be motorized control to cover both "hot spots."

Considering a haze profile derived from haze map can be different for a bare silicon wafer and a semiconductor manufacturer's wafer, different shapes and sizes of masks can be included for both the first mask 101 and the second mask 102.

Figure 5:
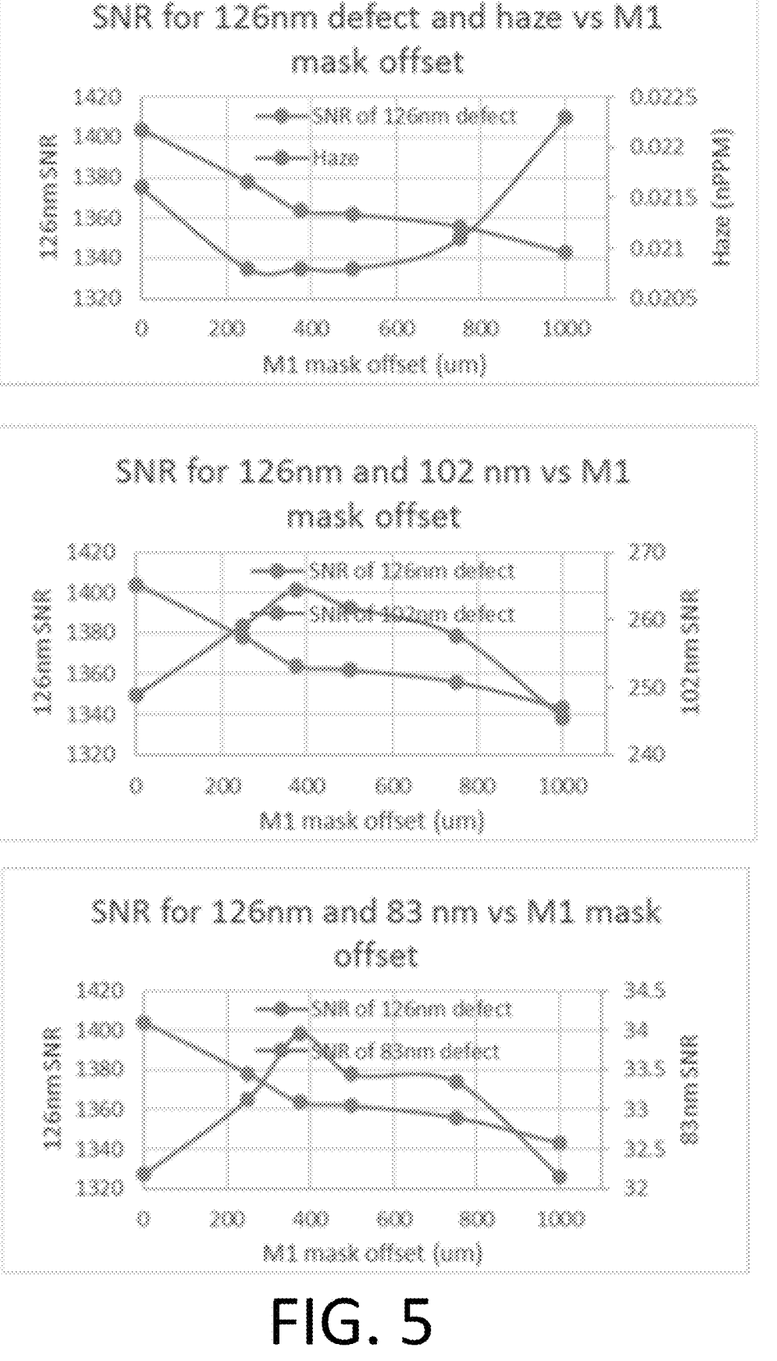
FIG. 5 is an example of searching for an optimal position of the second mask.

To determine an optimal location of the first mask 101 and second mask 102, a haze map for DW can be built by sweeping with the second mask 102 and the mask change wheel 108 switched to a slit. Then another mask on the mask change wheel 108 (such as the first mask 101) is controlled to sweep over certain range by monitoring signal-to-noise ratio and haze value. For example, the sweep may be less than 1 mm. From this information, an optimal first mask 101 position can be determined. To determine optimal first mask 101 position, one or more of minimal haze, highest signal-to-noise, and maximized sensitivity may be evaluated. Shown in FIG. 5 is one of example on how to search for the optimal position of second mask 102. To determine optimal second mask 102 position, one or more of minimal haze, highest signal-to-noise (SNR), and maximized sensitivity may be evaluated. M1 in FIG. 5 represents the second mask 102. By setting the second mask 102 to the optimal position, the similar procedure can be adopted for searching optimal position of the first mask 101 by sweeping the mask change wheel 108 over a certain range.

Turning back to FIG. 2, a processor 107 can be in electronic communication with the first actuator 105 and the second actuator 106. The processor 107 also can be in electronic communication with the collector 103. The processor 107 can be configured to determine a haze map of a wafer and send instructions to at least one of the first actuator 105 or the second actuator 106 to move at least one of the first mask 101 or the second mask 102 to compensate for haze on the haze map. Instructions to the first actuator 105 can move the first mask 101. Instructions to the second actuator 106 can move the second mask 102.

The processor 107 can be configured to send instructions to the second actuator 106 to sweep the second mask 102 over a range. The processor 107 then can be configured to monitor signal-to-noise ratio and haze values and determine an optimal position for the second mask 102. The optimal position can compensate for haze on the haze map, such as by minimizing the effect of haze to signal-to-noise.

The processor 107 also can be configured to send instructions to the first actuator 105 to sweep the first mask 101 over a range. The processor 107 then can be configured to monitor signal-to-noise ratio and haze values and determine an optimal position for the first mask. The optimal position can minimize haze value and push signal-to-noise higher, which can result in better sensitivity, such as by minimizing the effect of haze to signal-to-noise.

The processor 107 may be coupled to the components of the system 100 in any suitable manner (e.g., via one or more transmission media, which may include wired and/or wireless transmission media) such that the processor 107 can receive output. The processor 107 may be configured to perform a number of functions using the output. The system 100 can receive instructions or other information from the processor 107. The processor 107 optionally may be in electronic communication with a database, wafer inspection tool, a wafer metrology tool, or a wafer review tool (not illustrated) to receive additional information or to send instructions. For example, the processor 107 can be in electronic communication with a database that includes haze data for various wafers.

The processor 107, other system(s), or other subsystem(s) described herein may be part of various systems, including a personal computer system, image computer, mainframe computer system, workstation, network appliance, internet appliance, or other device. The subsystem(s) or system(s) may also include any suitable processor known in the art, such as a parallel processor. In addition, the subsystem(s) or system(s) may include a platform with high-speed processing and software, either as a standalone or a networked tool.

The processor 107 may be disposed in or otherwise part of the system 100 or another device. In an example, the processor 107 may be part of a standalone control unit or in a centralized quality control unit. Multiple processors 107 may be used.

The processor 107 may be implemented in practice by any combination of hardware, software, and firmware. Also, its functions as described herein may be performed by one unit, or divided up among different components, each of which may be implemented in turn by any combination of hardware, software and firmware. Program code or instructions for the processor 107 to implement various methods and functions may be stored in readable storage media.

If the system 100 includes more than one processor 107, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The processor 107 may be configured to perform a number of functions using the output of the system 100 or other output. For instance, the processor 107 may be configured to send the output to a storage medium. The processor 107 may be further configured as described herein.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The processor 107 may be configured according to any of the embodiments described herein. The processor 107 also may be configured to perform other functions or additional steps using the output of the system 100 or using images or data from other sources.

Various steps, functions, and/or operations of system 100 and the methods disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape, and the like. A carrier medium may include a transmission medium such as a wire, cable, or wireless transmission link. For instance, the various steps described throughout the present disclosure may be carried out by a single processor 107 or, alternatively, multiple processors 107. Moreover, different subsystems of the system 200 may include one or more computing or logic systems. Therefore, the above description should not be interpreted as a limitation on the present disclosure but merely an illustration.

Figure 6:
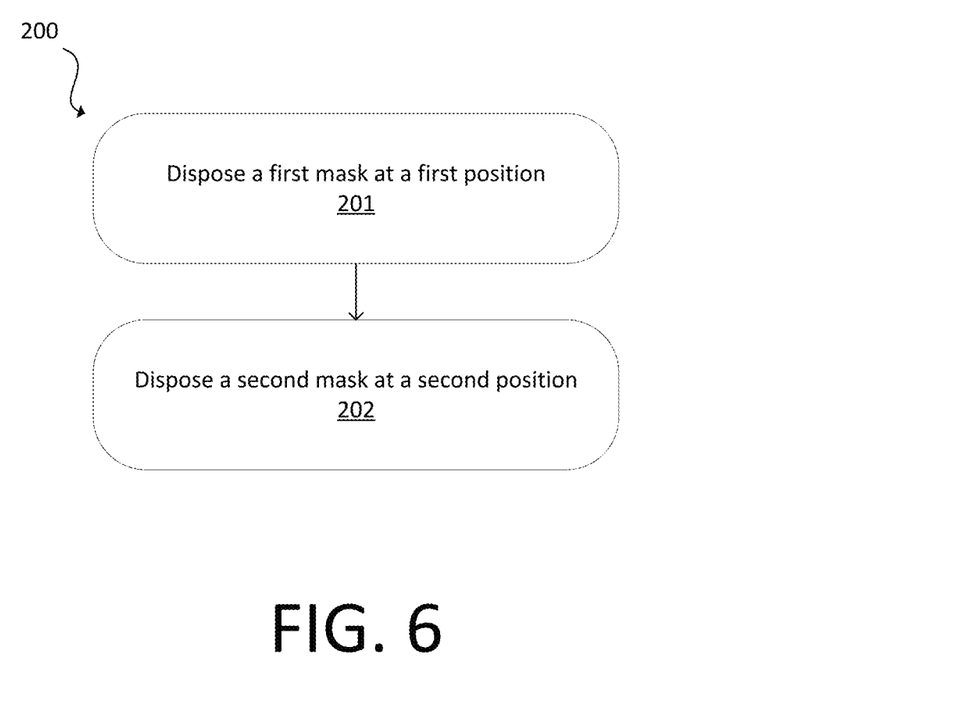
FIG. 6 is a flowchart of an embodiment of a method in accordance with the present disclosure.

FIG. 6 is a flowchart of an embodiment of a method 200. At 201, a first mask is disposed using a first actuator at a first position along a path of a light beam between a light source and a collector. The first mask defines a first aperture. At 202, a second mask is disposed at a second position using a second actuator along the path of the light beam between the first mask and the collector. The second mask defines a second aperture and is fabricated of metal. The first position and the second position minimize an effect of haze to signal-to-noise ratio.

Disposing the first mask can be independent of disposing the second mask. Disposing the first mask can include moving the first mask in a tangential direction. Disposing the second mask can include moving the second mask in a radial direction perpendicular to the tangential direction.

In an instance, a haze map of the wafer is determined using a processor. Instructions are sent to at least one of the first actuator and the second actuator to move at least one of the first mask or the second mask to compensate for haze on the haze map.

In another instance, instructions can be sent from the processor to the second actuator to sweep the second mask over a range. Using the processor, the signal-to-noise ratio and haze values is monitored and an optimal position for the second mask is determined.

Instructions can be sent from the processor to the first actuator to sweep the first mask over a range. Using the processor, monitoring, using the processor, the signal-to-noise ratio and haze values are monitored and an optimal position for the first mask is determined.

In an example, a series of masks are added to the mask change wheel 108 with the first mask 101 to evaluate the impact of haze to signal-to-noise ratio. With certain masks using embodiments disclosed herein, the haze can be suppressed to almost 30x and signal-to-noise ratio is improved. In an instance, the optimal combination can be achieved with a few iterative independent optimizations of the first mask and the second mask. The start points of the first mask and the second mask may be near one another at initial alignment.

With respect to the W2 UV channel, there are typically three channels for UV, W1, W2 and Narrow. The W2 UV channel is shown in FIG. 2, which is shared with DW channel.

The embodiments disclosed herein are teachable for tangential and radial directions, which makes the system adaptive to a variation of haze "hot spots" shift from tool to tool. Searching of an optimal position of the first mask 101 and the second mask 102 can be combined with initial calibration. The initial calibration can be performed once. Additional calibration may not be needed.

The embodiments of the first mask 101 and second mask 102 can be retrofitted onto existing tools.

Figure 7:
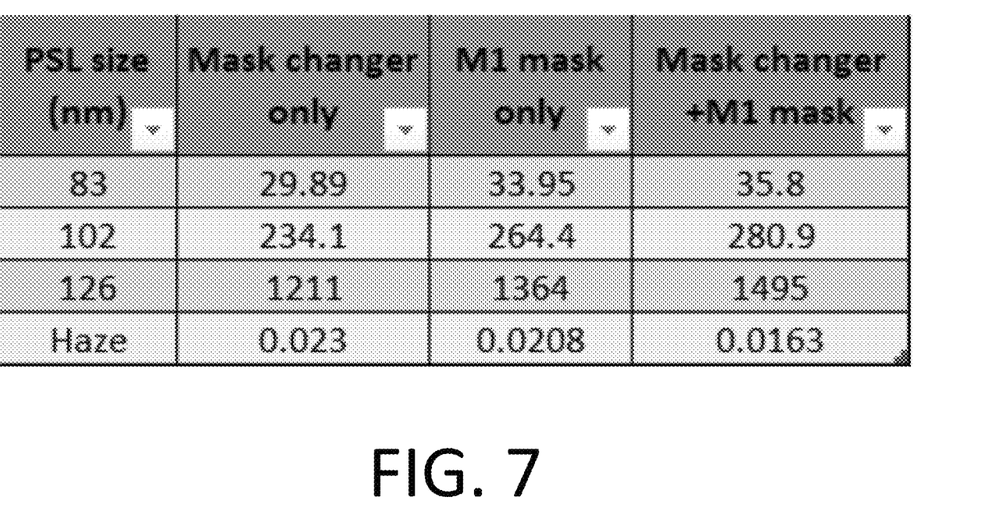
FIG. 7 includes a table showing experimental results.

Embodiments disclosed herein can solve the "high haze" issue of UV normal narrow channel, which has caused problems with previous systems. High haze refers to the haze value during the normal scan. The similar design can be used for a narrow channel. A UV narrow channel has suffered high haze and thus less desired sensitivity. This dynamic and adaptive haze mask has been proven to suppress the haze, improve signal-to-noise ratio, and sensitivity of DW. The resultant haze suppression and signal-to-noise ratio improvement is shown in the table of FIG. 7. The table in FIG. 7 shows the signal-to-noise improvement of a known defect size, which is shown in the left column with different combinations of masks disclosed herein. Information in the table can be used to determine effectiveness of a mask combination.

Each of the steps of the method may be performed as described herein. The methods also may include any other step(s) that can be performed by the processor and/or computer subsystem(s) or system(s) described herein. The steps can be performed by one or more computer systems, which may be configured according to any of the embodiments described herein. In addition, the methods described above may be performed by any of the system embodiments described herein.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A system comprising:
    an illumination subsystem that generates a light beam;
    a stage configured to hold a wafer in a path of the light beam;
    a collector in the path of the light beam;
    a first mask disposed along the path of the light beam between the light source and the collector, wherein the first mask defines a first aperture;
    a first actuator that moves the first mask along a tangential direction;
    a second mask disposed along the path of the light beam between the first mask and the collector, wherein the second mask is fabricated of metal and defines a second aperture; and
    a second actuator that moves the second mask along a radial direction perpendicular to the tangential direction, wherein the first mask and the second mask are independently movable along the tangential direction and the radial direction, respectively, using the first actuator and the second actuator to minimize an effect of haze to signal-to-noise ratio.

2. The system of claim 1, further comprising a processor in electronic communication with the first actuator and the second actuator.

3. The system of claim 2, wherein the processor is configured to:
    determine a haze map of the wafer; and
    send instructions to at least one of the first actuator and the second actuator to move at least one of the first mask or the second mask.

4. The system of claim 3, wherein the processor is further configured to:
    send instructions to the second actuator to sweep the second mask over a range;
    monitor signal-to-noise ratio and haze values; and
    determine an optimal position for the second mask that minimizes the effect of haze to signal-to-noise.

5. The system of claim 3, wherein the processor is further configured to:
    send instructions to the first actuator to sweep the first mask over a range;
    monitor signal-to-noise ratio and haze values; and
    determine an optimal position for the first mask that minimizes the effect of haze to signal-to-noise.

6. The system of claim 1, wherein the first actuator includes a mask change wheel.

7. The system of claim 1, wherein the first mask is disposed on a mask change wheel, and wherein the mask change wheel includes a plurality of other masks.

8. A method comprising:
    disposing, using a first actuator, a first mask at a first position along a path of a light beam between a light source and a collector, wherein the first mask defines a first aperture;
    disposing, using a second actuator, a second mask at a second position along the path of the light beam between the first mask and the collector, wherein the second mask is fabricated of metal and wherein the second mask defines a second aperture; and
    wherein the first position and the second position minimize an effect of haze to signal-to-noise ratio.

9. The method of claim 8, wherein disposing the first mask is independent of disposing the second mask.

10. The method of claim 8, further comprising:
    determining, using a processor, a haze map of the wafer; and
    sending instructions, using the processor, to at least one of the first actuator and the second actuator to move at least one of the first mask or the second mask to compensate for haze on the haze map.

11. The method of claim 10, further comprising:
    sending instructions from the processor to the second actuator to sweep the second mask over a range;
    monitoring, using the processor, the signal-to-noise ratio and haze values; and
    determining, using the processor, an optimal position for the second mask that minimizes the effect of haze to signal-to-noise.

12. The method of claim 10, further comprising:
    sending instructions from the processor to the first actuator to sweep the first mask over a range;
    monitoring, using the processor, the signal-to-noise ratio and haze values; and
    determining, using the processor, an optimal position for the first mask that minimizes the effect of haze to signal-to-noise.

13. The method of claim 8, wherein disposing the first mask includes moving the first mask in a tangential direction.

14. The method of claim 13, wherein disposing the second mask includes moving the second mask in a radial direction perpendicular to the tangential direction.

* * * * *